(12) United States Patent
Torrianni et al.

(10) Patent No.: US 10,973,630 B2
(45) Date of Patent: Apr. 13, 2021

(54) ANTI-PARAVALVULAR LEAKAGE COMPONENT FOR A TRANSCATHETER VALVE PROSTHESIS

(71) Applicant: MEDTRONIC CV LUXEMBOURG S.A.R.L., Luxembourg (LU)

(72) Inventors: Mark Torrianni, San Juan Capistrano, CA (US); Eric Richardson, Santa Ana, CA (US); Kshitija Garde, Santa Ana, CA (US)

(73) Assignee: MEDTRONIC CV LUXEMBOURG S.A.R.L., Luxembourg (LU)

( * ) Notice: Subject to any disclaimer, the term of this patent is extended or adjusted under 35 U.S.C. 154(b) by 16 days.

(21) Appl. No.: 16/571,456

(22) Filed: Sep. 16, 2019

(65) Prior Publication Data

US 2020/0008935 A1    Jan. 9, 2020

Related U.S. Application Data

(62) Division of application No. 13/757,380, filed on Feb. 1, 2013, now Pat. No. 10,413,401.

(51) Int. Cl.
*A61F 2/24*    (2006.01)

(52) U.S. Cl.
CPC .......... *A61F 2/2409* (2013.01); *A61F 2/2418* (2013.01); *A61F 2220/005* (2013.01);
(Continued)

(58) Field of Classification Search
CPC .................. A61F 2/24; A61F 2/2409
See application file for complete search history.

(56) References Cited

U.S. PATENT DOCUMENTS

| | | |
|---|---|---|
| 5,571,175 A | 11/1996 | Vanney et al. |
| 7,276,078 B2 | 10/2007 | Spenser et al. |

(Continued)

FOREIGN PATENT DOCUMENTS

| | | |
|---|---|---|
| EP | 0537487 | 4/1993 |
| EP | 0537487 B1 | 4/1993 |

(Continued)

OTHER PUBLICATIONS

EPC communication issued in European Application No. 15723578.9, dated Sep. 6, 2018.
(Continued)

*Primary Examiner* — Matthew W Schall
(74) *Attorney, Agent, or Firm* — Medler Ferro Woodhouse & Mills PLLC

(57) ABSTRACT

A transcatheter valve prosthesis includes an expandable tubular stent, a prosthetic valve within the stent, and an anti-paravalvular leakage component coupled to and encircling the tubular stent. The anti-paravalvular leakage component includes a radially-compressible annular scaffold, which is a sinusoidal patterned ring of self-expanding material, and an impermeable membrane extending over the annular scaffold. The anti-paravalvular leakage component has an expanded configuration in which at least segments of the annular scaffold curve radially away from the tubular stent. Alternatively, the anti-paravalvular leakage component includes a plurality of self-expanding segments and an annular sealing element coupled to inner surfaces of the segments. The anti-paravalvular leakage component has an expanded configuration in which the segments curve radially away from the tubular stent and the annular sealing element is positioned between an outer surface of the tubular stent and inner surfaces of the segments.

9 Claims, 12 Drawing Sheets

(52) U.S. Cl.
CPC . *A61F 2230/008* (2013.01); *A61F 2230/0013* (2013.01); *A61F 2250/0069* (2013.01)

(56) References Cited

U.S. PATENT DOCUMENTS

| | | |
|---|---|---|
| 7,331,991 B2 | 2/2008 | Kheradvar et al. |
| 7,628,805 B2 | 12/2009 | Spenser et al. |
| 7,708,775 B2 | 5/2010 | Rowe et al. |
| 7,780,725 B2 | 8/2010 | Haug et al. |
| 8,002,825 B2 | 8/2011 | Letac et al. |
| 8,182,528 B2 | 5/2012 | Salahieh et al. |
| 8,231,670 B2 | 7/2012 | Salahieh et al. |
| 8,449,599 B2 | 5/2013 | Chau et al. |
| 8,603,160 B2 | 12/2013 | Salahieh et al. |
| 8,623,078 B2 | 1/2014 | Salahieh et al. |
| 8,628,566 B2 | 1/2014 | Eberhardt et al. |
| 8,641,757 B2 | 2/2014 | Pintor et al. |
| 8,668,733 B2 | 3/2014 | Salahieh et al. |
| 8,673,000 B2 | 3/2014 | Tabor et al. |
| 8,734,484 B2 | 5/2014 | Ahlberg et al. |
| 8,795,357 B2 | 8/2014 | Yohanan et al. |
| 8,801,706 B2 | 8/2014 | Rothstein et al. |
| 8,802,356 B2 | 8/2014 | Braido et al. |
| 8,808,356 B2 | 8/2014 | Braido et al. |
| 2003/0199963 A1 | 10/2003 | Tower et al. |
| 2003/0199971 A1 | 10/2003 | Tower et al. |
| 2004/0030381 A1 | 2/2004 | Shu |
| 2004/0111111 A1 | 6/2004 | Lin |
| 2004/0122514 A1 | 6/2004 | Fogarty et al. |
| 2006/0004442 A1 | 1/2006 | Spenser et al. |
| 2007/0270944 A1 | 11/2007 | Bergheim et al. |
| 2007/0293944 A1 | 12/2007 | Spenser |
| 2008/0243245 A1 | 10/2008 | Thambar |
| 2009/0099653 A1 | 4/2009 | Suri et al. |
| 2009/0112311 A1 | 4/2009 | Miles et al. |
| 2009/0192591 A1 | 7/2009 | Ryan et al. |
| 2010/0036479 A1 | 2/2010 | Hill et al. |
| 2010/0168839 A1 | 7/2010 | Braido et al. |
| 2010/0168844 A1 | 7/2010 | Toomes et al. |
| 2010/0198238 A1 | 8/2010 | Sorajja |
| 2010/0277413 A1 | 11/2010 | Wang et al. |
| 2010/0280589 A1 | 11/2010 | Styrc |
| 2011/0054466 A1 | 3/2011 | Rothstein et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0245911 A1 | 10/2011 | Quill et al. |
| 2011/0257721 A1 | 10/2011 | Tabor |
| 2011/0264206 A1 | 10/2011 | Tabor |
| 2012/0022633 A1 | 1/2012 | Olson et al. |
| 2012/0041549 A1 | 2/2012 | Salahieh et al. |
| 2012/0041550 A1 | 2/2012 | Salahieh et al. |
| 2013/0190857 A1 | 7/2013 | Mitra et al. |
| 2013/0190862 A1 | 7/2013 | Pintor et al. |
| 2013/0197622 A1 | 8/2013 | Mitra et al. |
| 2013/0304200 A1 | 11/2013 | McLean et al. |
| 2013/0331929 A1 | 12/2013 | Mitra et al. |
| 2014/0046426 A1 | 2/2014 | Kovalsky |
| 2014/0114402 A1 | 4/2014 | Ahlberg et al. |
| 2014/0114406 A1 | 4/2014 | Salahieh et al. |
| 2014/0194975 A1 | 7/2014 | Quill et al. |
| 2014/0194981 A1 | 7/2014 | Menk et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0243969 A1 | 8/2014 | Venkatasubramanian et al. |
| 2014/0257475 A1 | 9/2014 | Gross et al. |
| 2014/0277388 A1 | 9/2014 | Skemp |
| 2014/0277413 A1 | 9/2014 | Richter et al. |
| 2014/0277417 A1 | 9/2014 | Schraut et al. |
| 2014/0277419 A1 | 9/2014 | Garde et al. |
| 2014/0277423 A1 | 9/2014 | Alkhatib et al. |
| 2014/0277424 A1 | 9/2014 | Oslund |
| 2014/0277425 A1 | 9/2014 | Dakin |
| 2014/0277426 A1 | 9/2014 | Dakin et al. |
| 2014/0277428 A1 | 9/2014 | Skemp et al. |

FOREIGN PATENT DOCUMENTS

| | | |
|---|---|---|
| WO | 2009/094501 A1 | 7/2009 |
| WO | WO2009/094501 | 7/2009 |
| WO | 2011/051043 A1 | 5/2011 |
| WO | WO2011/051043 | 5/2011 |
| WO | 2013/033791 A1 | 3/2013 |
| WO | 2013/037519 A1 | 3/2013 |
| WO | WO2013/033791 | 3/2013 |
| WO | WO2013/037519 | 3/2013 |
| WO | 2013/059747 A1 | 4/2013 |
| WO | WO2013/059747 | 4/2013 |
| WO | WO20030304200 | 11/2013 |
| WO | 2014/072439 A1 | 5/2014 |
| WO | WO2014072439 | 5/2014 |

OTHER PUBLICATIONS

"Invitation to Pay Additional Fees", International application No. PCT/US2014/010734, including annex with Partial International Search Report, dated Apr. 9, 2014.

"International Search Report and Written Opinion", International Application No. PCT/2014/014090, dated Apr. 14, 2014.

EPC communication dated Sep. 6, 2018 in corresponding EP Appln.No. 15 723 578.9.

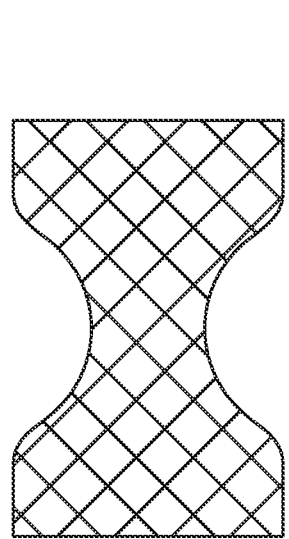
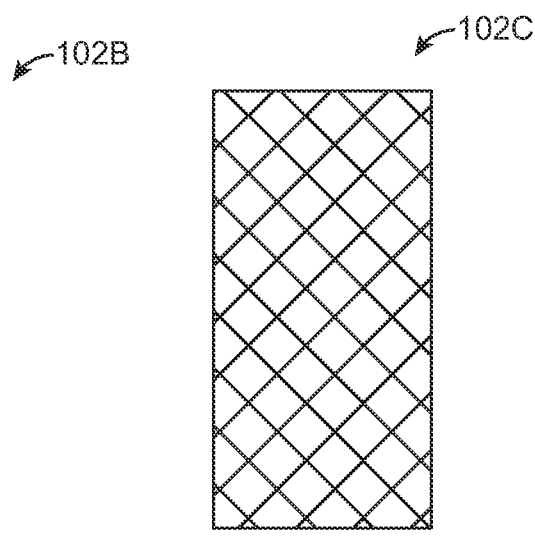
FIG. 1B        FIG. 1C
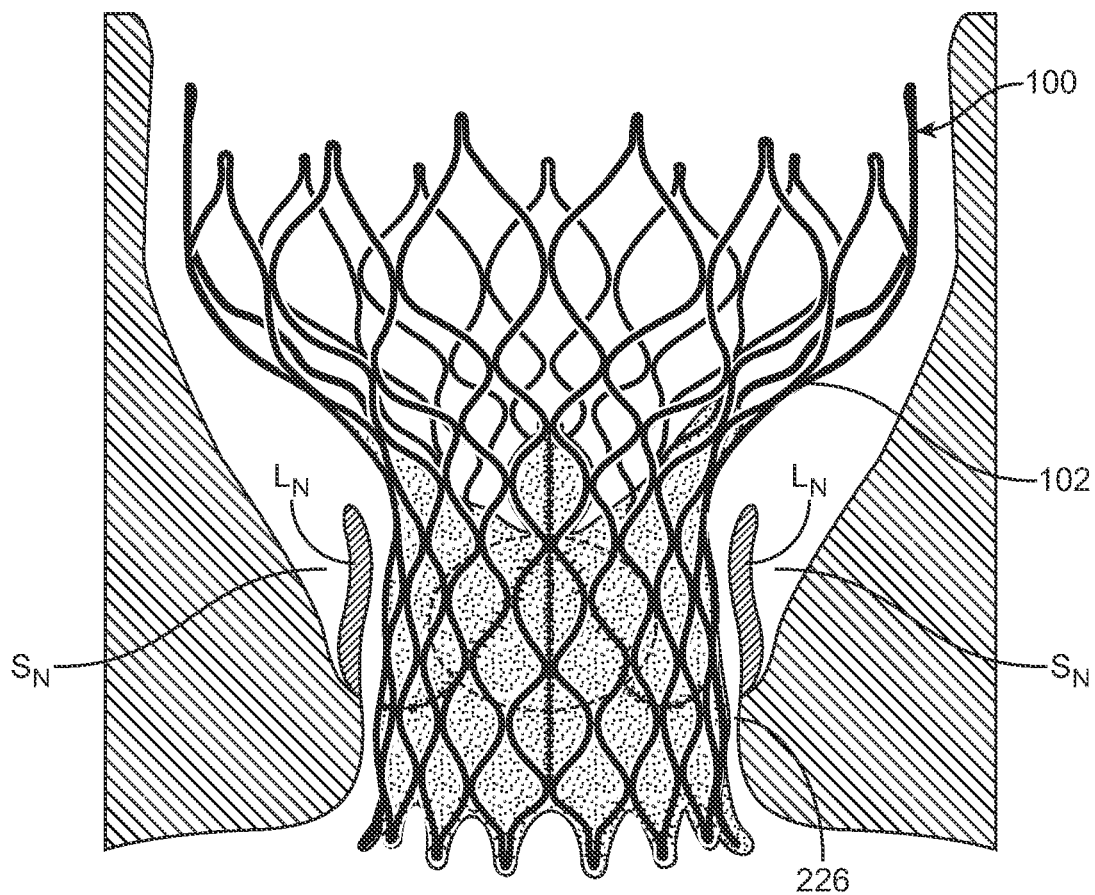
FIG. 2

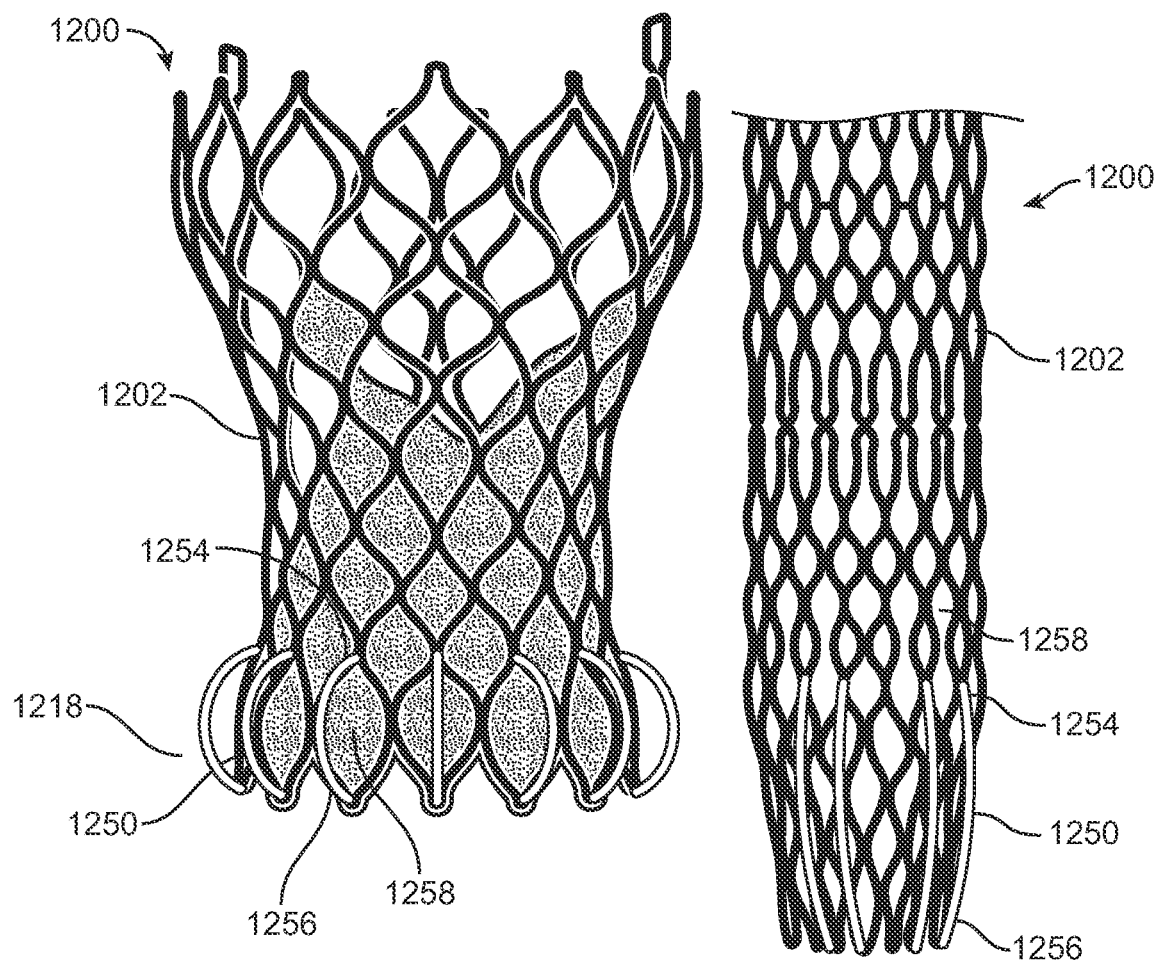
FIG. 13     FIG. 14
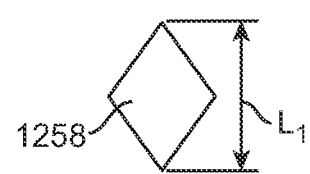  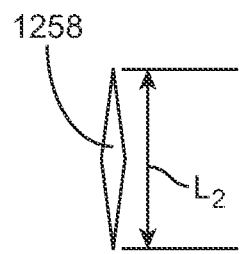
FIG. 13A    FIG. 14A

ANTI-PARAVALVULAR LEAKAGE COMPONENT FOR A TRANSCATHETER VALVE PROSTHESIS

CROSS-REFERENCE TO RELATED APPLICATION

This application is a divisional of U.S. application Ser. No. 13/757,380, filed Feb. 1, 2013, the disclosure of which is incorporated by reference herein in its entirety.

FIELD OF THE INVENTION

The present invention relates to transcatheter valve prostheses and methods of preventing paravalvular leakage. More specifically, the present invention relates to an anti-paravalvular leakage component integrated on an outer surface of a transcatheter valve prosthesis to seal gaps between a support frame of the prosthesis and native valve tissue.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the mitral valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to anti-paravalvular leakage components coupled to an outer surface of the valve prosthesis to seal gaps between the valve prosthesis and native valve tissue.

BRIEF SUMMARY OF THE INVENTION

Embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a radially-compressible annular scaffold and a membrane of impermeable material extending over an outer surface of the annular scaffold. The annular scaffold is a sinusoidal patterned ring of self-expanding material and includes a plurality of peaks, a plurality of valleys, and a plurality of segments with opposing peaks and valleys being formed between a pair of adjacent segments. The anti-paravalvular leakage component has an expanded configuration in which at least the plurality of segments curve radially away from the outer surface of the tubular stent.

According to another embodiment hereof, transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a plurality of self-expanding segments and an annular sealing element coupled to inner surfaces of the segments. A first end and a second end of each segment are coupled to the outer surface of the tubular stent. The anti-paravalvular leakage component has an expanded configuration in which the segments curve radially away from the outer surface of the tubular stent and the annular sealing element is positioned between an outer surface of the tubular stent and inner surfaces of the segments.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1B is a side view illustration of an alternative configuration of a heart valve prosthesis for use in embodiments hereof.

FIG. 1C is a side view illustration of an alternative configuration of a heart valve prosthesis for use in embodiments hereof.

FIG. 2 is a side view illustration of the heart valve prosthesis of FIG. 1 implanted within a native valve annulus.

FIG. 13 is side view of the heart valve prosthesis of FIG. 12 in a deployed or expanded configuration, with the annular sealing element removed for clarity.

FIG. 13A illustrates the length of a diamond-shaped opening of a stent when the heart valve prosthesis of FIG. 13 is in a deployed or expanded configuration.

FIG. 14 is a side view of the heart valve prosthesis of FIG. 13 in a compressed or delivery configuration.

FIG. 14A illustrates the length of a diamond-shaped opening of a stent when the heart valve prosthesis of FIG. 13 is in a compressed or delivery configuration.

DETAILED DESCRIPTION OF THE INVENTION

Specific embodiments of the present invention are now described with reference to the figures, wherein like reference numbers indicate identical or functionally similar elements. If utilized herein, the terms "distal" or "distally" refer to a position or in a direction away from the heart and the terms "proximal" and "proximally" refer to a position near or in a direction toward the heart. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
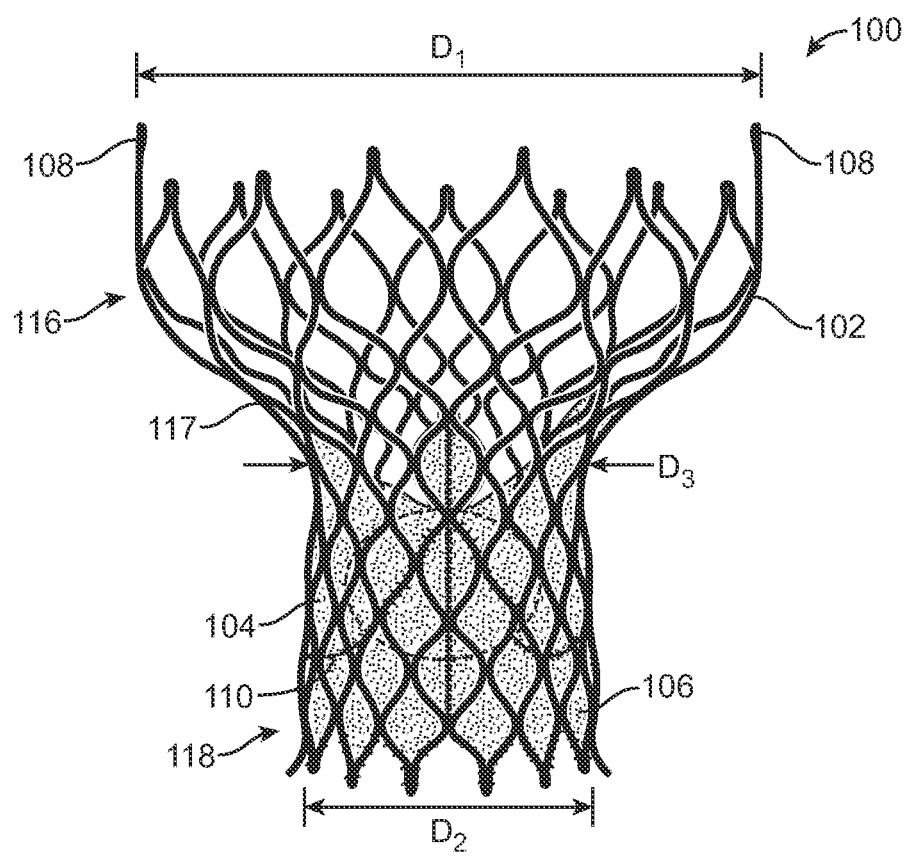
FIG. 1 is a side view illustration of an exemplary transcatheter heart valve prosthesis for use in embodiments hereof.

FIG. 1 depicts an exemplary transcatheter heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 includes an expandable stent or frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. Alternatively, heart valve prosthesis 100 may be balloon-expandable as would be understood by one of ordinary skill in the art.

Figure 1A:
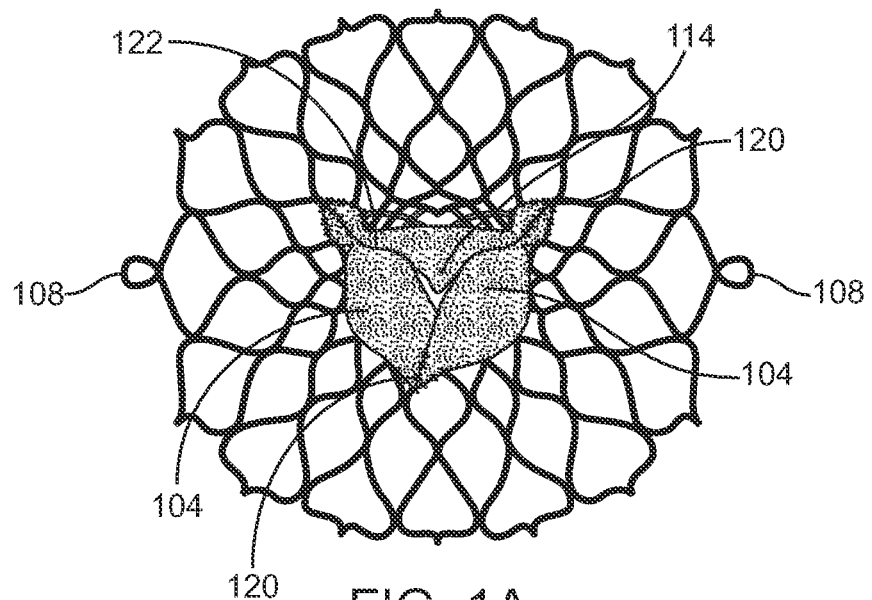
FIG. 1A is a top view illustration of the heart valve prosthesis of FIG. 1.

In the embodiment depicted in FIGS. 1 and 1A, stent 102 of valve prosthesis 100 has a deployed asymmetric hourglass configuration including an enlarged first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102 may be designed with a number of different configurations and sizes to meet the different requirements of the location in which it may be implanted. When configured as a replacement for an aortic valve, second section 118 functions as an inflow end of heart valve prosthesis 100 and extends into and anchors within the aortic annulus of a patient's left ventricle, while first section 116 functions as an outflow end of heart valve prosthesis 100 and is positioned in the patient's ascending aorta. When configured as a replacement for a mitral valve, enlarged first section 116 functions as an inflow end of heart valve prosthesis 100 and is positioned in the patient's left atrium, while second section 118 functions as an outflow end of heart valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed asymmetric hourglass configuration of FIGS. 1 and 1A, the stent/valve support frame may have a symmetric hourglass configuration 102B shown in FIG. 1B, a generally tubular configuration 102C as shown in FIG. 1C, or other stent configuration or shape known in the art for valve replacement. Stent 102 also may include eyelets 108 that extend from first end 116 thereof for use in loading the heart valve prosthesis 100 into a delivery catheter (not shown).

As previously mentioned, heart valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration may alternatively be used in embodiments hereof. More particularly, if heart valve prosthesis 100 is configured for placement within a native valve having three leaflets such as the aortic, tricuspid, or pulmonary valves, heart valve prosthesis 100 includes three valve leaflets 104. If heart valve prosthesis 100 is configured for placement within a native valve having two leaflets such as the mitral valve, heart valve prosthesis 100 includes two valve leaflets 104. Valve leaflets 104 are sutured or otherwise securely and sealingly attached to the interior surface of stent 102 and/or graft material 106 which encloses or lines stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Delivery of heart valve prosthesis 100 may be accomplished via a percutaneous transfemoral approach or a transapical approach directly through the apex of the heart via a thoracotomy, or may be positioned within the desired area of the heart via different delivery methods known in the art for accessing heart valves. During delivery, if self-expanding, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve. Alternatively, heart valve prosthesis 100 may be balloon-expandable and delivery thereof may be accomplished via a balloon catheter as would be understood by one of ordinary skill in the art.

FIG. 2 is a side view illustration of heart valve prosthesis 100 implanted within a native heart valve, which is shown in section, having native leaflets LN and corresponding native sinuses SN. When heart valve prosthesis 100 is deployed within the valve annulus of a native heart valve, stent 102 expands within native valve leaflets LN of the patient's defective valve, retaining the native valve leaflets in a permanently open state. The native valve annulus may include surface irregularities on the inner surface thereof, and as a result one or more gaps or cavities/crevices 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 3:
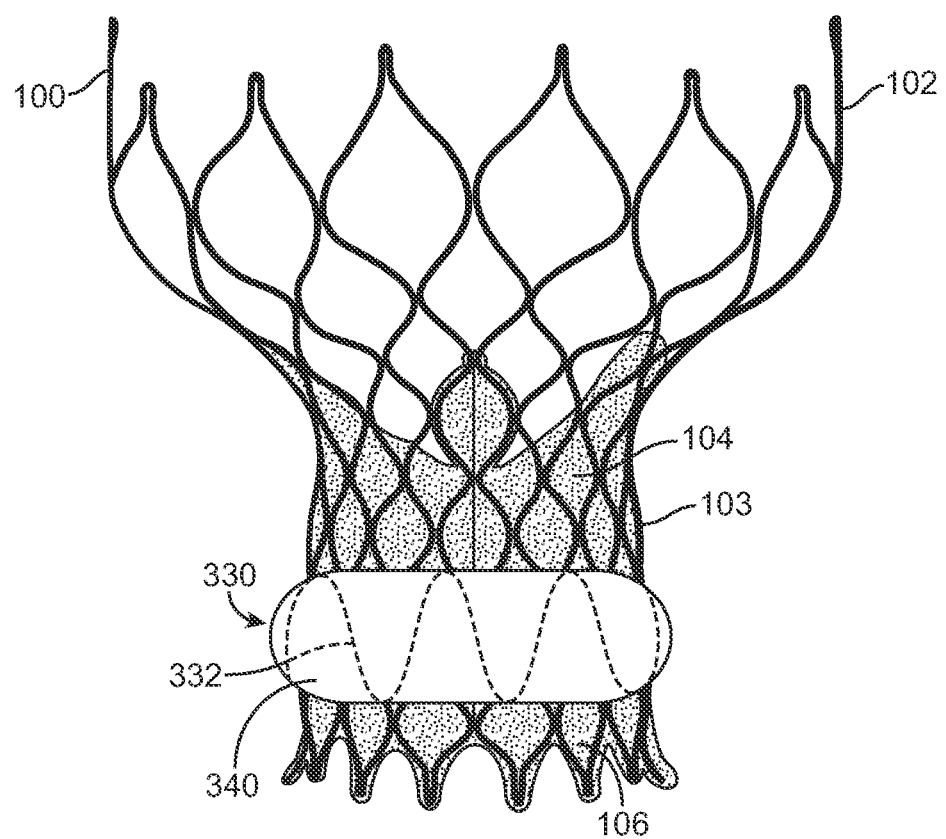
FIG. 3 is a side view of the heart valve prosthesis of FIG. 1 having an anti-paravalvular leakage component coupled thereto, wherein the anti-paravalvular leakage component includes a annular scaffold and an impermeable membrane that covers an outer surface of the annular scaffold.

Embodiments hereof relate to methods for delivering a heart valve prosthesis having a self-expanding anti-paravalvular leakage component thereon that functions to occlude or fill gaps between the perimeter of a heart valve prosthesis and the native valve annulus, thereby reducing, minimizing, or eliminating leaks there through. An anti-paravalvular leakage component 330 is shown in FIG. 3 in its deployed or expanded configuration, extending around an outer surface or perimeter 103 of heart valve prosthesis 100 to prevent paravalvular leakage in situ. Anti-paravalvular leakage component 330 extends in a radially outward direction relative to outer surface 103 of heart valve prosthesis 100, and exerts a radial pressure onto a native valve annulus when deployed in situ. More particularly, an expanded or deployed outer diameter of anti-paravalvular leakage component 330 is predetermined to be greater than the expanded outer diameter of stent 102. When deployed, anti-paravalvular leakage component 330 radially expands into and substantially fills any/all gaps or cavities/crevices between outer surface 103 of stent 102 and native valve tissue. "Substantially" as utilized herein means that blood flow through the target gap or cavity is occluded or blocked, or stated another way blood is not permitted to flow there through. Anti-paravalvular leakage component 330 blocks blood flow around the outer perimeter of prosthesis 100, thereby minimizing and/or eliminating any paravalvular leakage at the implantation site.

More particularly, anti-paravalvular leakage component 330 includes a radially-compressible ring or annular scaffold 332 (shown in phantom in FIG. 3) that is operable to self-expand and an impermeable membrane 340 that covers or extends over an outer surface of annular scaffold 332. Annular scaffold 332 is shown removed from anti-paravalvular leakage component 330 in FIG. 4. In addition, FIG. 5 shows annular scaffold 332 laid flat out for illustrative purposes, while FIG. 5A is a cross-sectional view taken along line A-A of FIG. 5. Annular scaffold 332 has sufficient radial spring force and flexibility to conformingly engage impermeable membrane 340 within a native heart valve annulus. Suitable materials for impermeable membrane 340 include but are not limited to a low-porosity woven fabric, such as polyester, Dacron fabric, or PTFE. Porous materials advantageously provide a medium for tissue ingrowth. Further, impermeable membrane 340 may be pericardial tissue or may be a knit or woven polyester, such as a polyester or PTFE knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side. Impermeable membrane 340 is coupled to annular scaffold 332 via sutures or other suitable mechanical connection.

Figure 4:
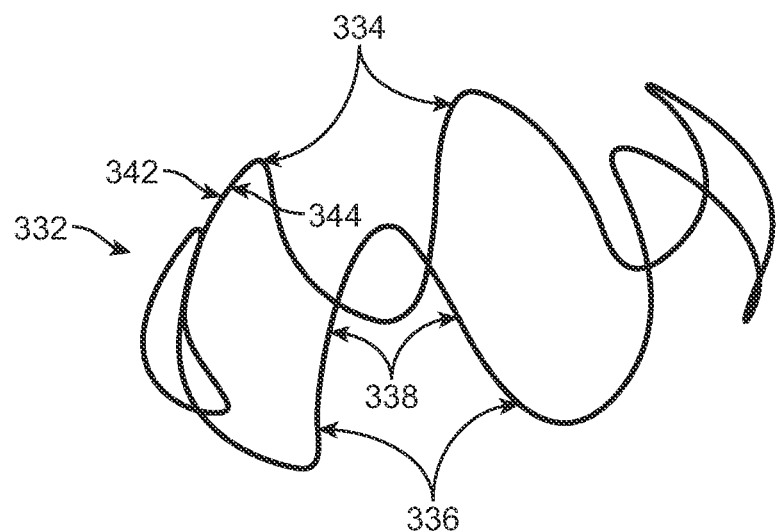
FIG. 4 is a perspective view of the annular scaffold of the anti-paravalvular leakage component of FIG. 3.
Figure 5:
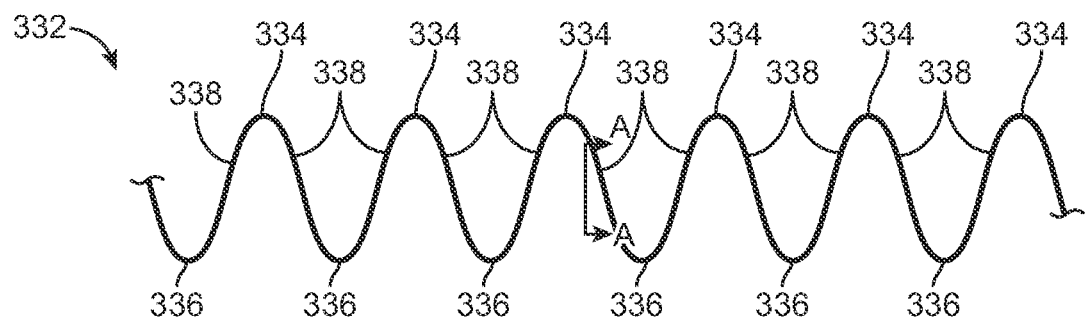
FIG. 5 illustrates the annular scaffold of the anti-paravalvular leakage component of FIG. 3 laid flat out for illustrative purposes.
Figure 5A:
FIG. 5A is a cross-sectional view taken along line A-A of FIG. 5.
Figure 7:
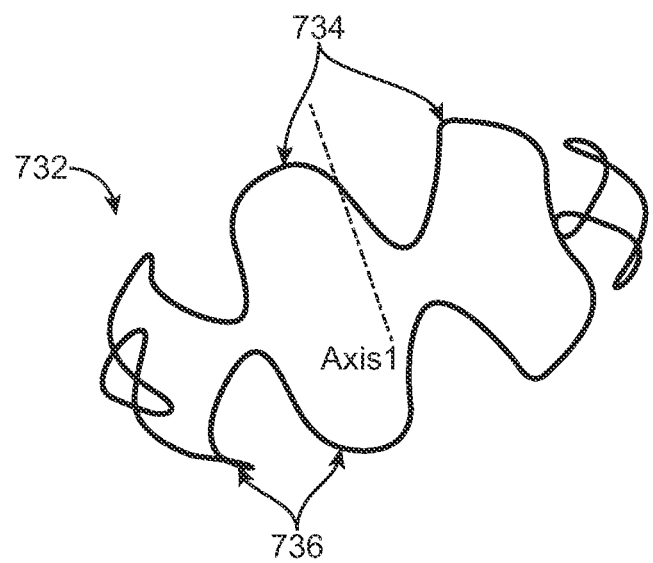
FIG. 7 is a perspective view of an annular scaffold for use in an anti-paravalvular leakage component, according to another embodiment hereof, wherein the annular scaffold includes an increased number of peaks and valleys relative to the annular scaffold of FIG. 4.

With reference to FIGS. 4 and 5, annular scaffold 332 is a sinusoidal patterned ring a plurality of peaks 334, a plurality of valleys 336, and a plurality of segments 338 with peaks 334 and valleys 336 being formed between a pair of adjacent segments 338 as shown in FIG. 4. Peaks and valleys 334, 336 are bends or turns of the scaffold having opposing orientations. In the embodiment depicted in FIGS. 4 and 5, annular scaffold 332 includes six peaks 334 and six valleys 336. However, it would be obvious to one of ordinary skill in the art that the annular scaffold may include a higher or lower number of peaks and valleys. For example, FIG. 7 illustrates an embodiment in which an annular scaffold 732 includes eight peaks 734 and eight valleys 736. Conformability of the annular scaffold increases with a higher or increased number of peaks and valleys; however, the annular scaffold is more radially-compressible or collapsible for delivery with a lower or decreased number of peaks and valleys. In an embodiment, the annular scaffold includes between four and eighteen pairs of peaks and valleys.

In the embodiment depicted in FIG. 3, segments 338 bow or curve radially outward while both peaks 332 and valleys 334 bend or curve radially inward toward stent 102. Outer surface 342 of each segment 338 is convex, while an inner surface 344 of each segment 338 is concave. In one embodiment hereof, only peaks 332 are coupled to stent 102 while valleys 334 are unattached or free. In another embodiment hereof, only valleys 334 are coupled to stent 102 while peaks 332 are unattached or free. When only one end of annular scaffold 332 is constrained, i.e., either peaks 332 or valleys 334, the opposing unattached or free end of the annular scaffold is unconstrained, highly flexible, and has an ability to conform to an outer sheath utilized in deployment thereof. More particularly, the unattached peaks or valleys of the annular scaffold slide or ride along outer surface 103 of stent 102 when an outer sheath is advanced over the stent to compress/collapse heart valve prosthesis 100 for delivery. By sliding along outer surface 103 of stent 102, annular scaffold 332 and therefore anti-paravalvular leakage component 330 approaches a substantially linear delivery configuration within the outer sheath. When the outer sheath is retracted to deploy heart valve prosthesis 100, the unattached or free peaks or valleys of the annular scaffold return to their preset expanded or deployed shape because annular scaffold 332 is formed from a material having a mechanical memory. Mechanical memory may be imparted to annular scaffold 332 by thermal treatment to achieve a spring temper in stainless steel, for example, or to set a shape memory in a susceptible metal alloy, such as NiTi (Nitinol). In an alternate embodiment, a mechanical memory to return to the preset expanded or deployed shape may be imparted to a shape memory polymer that forms annular scaffold 332, such as any of the polymers disclosed in U.S. Pat. Appl. Pub. No. 2004/0111111 to Lin, which is herein incorporated by reference in its entirety.

In an embodiment, anti-paravalvular leakage component 330 is coupled to heart valve prosthesis 100 after manufacture of heart valve prosthesis 100. In another embodiment, anti-paravalvular leakage component 330 is manufactured in conjunction with, i.e., at the same time as, heart valve prosthesis 100. Regardless of whether anti-paravalvular leakage component 330 is formed concurrently with or subsequent to heart valve prosthesis 100, annular scaffold 332 of anti-paravalvular leakage component 330 may be formed from a single, continuous wire that may be solid or hollow and may have a different cross-section and/or size from stent 102 of heart valve prosthesis 100. More particularly, in an embodiment, stent 102 is formed via laser-cut manufacturing method and therefore a strut of the stent may have a non-circular cross-section, e.g., a square, rectangular, or polygonal cross-section, and a thickness ranging between 0.011-0.018 inches. Annular scaffold 332 may be formed from a single, continuous wire having a circular or round cross-section as shown in FIG. 5A with a diameter between 0.005-0.015 inches. In another embodiment, the cross-section of the wire that forms annular scaffold 332 may be an oval, elliptical, rectangular or ribbon-like, or any other suitable shape. By forming annular scaffold 332 of a relatively thinner or smaller wire as compared to a strut of stent 102, annular scaffold 332 has greater flexibility to conform to the inner surface of the native valve annulus including any surface irregularities that may be present, thereby filling any gaps or cavities/crevices that may be present between the heart valve prosthesis 100 and native tissue, while the thicker struts of stent 102 provide sufficient radial force to deploy the heart valve prosthesis into apposition with the native valve annulus. In another embodiment hereof, annular scaffold 332 of anti-paravalvular leakage component 330 may be integrally formed with stent 102 of heart valve prosthesis via a laser-cut manufacturing method. If integrally formed with stent 102, the cross-section of the wire/strut of annular scaffold 332 may be the same size and shape as a strut of the stent or may be of a different size and/or shape as the strut of the stent.

Figure 6:
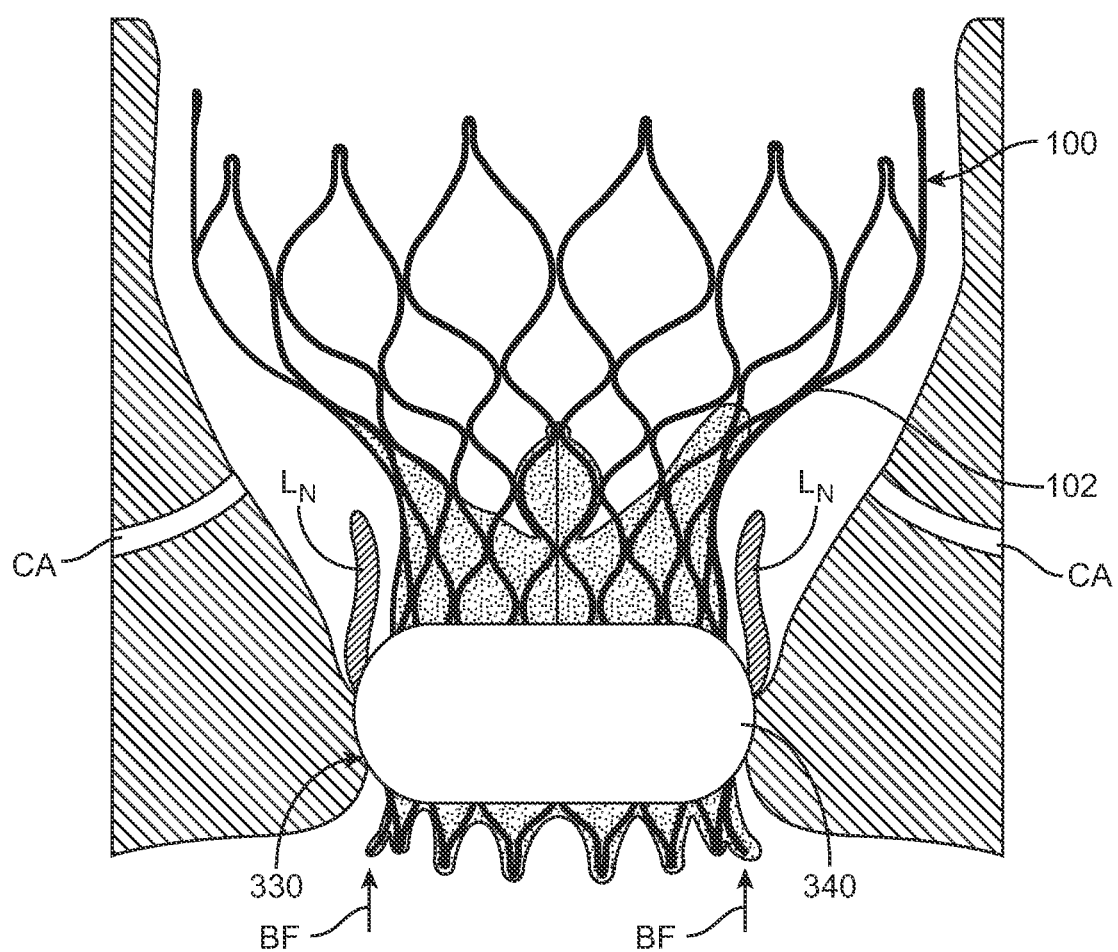
FIG. 6 is a side view illustration of the heart valve prosthesis of FIG. 3, having an anti-paravalvular leakage component coupled thereto, implanted within a native valve annulus.

Shown deployed within an aortic valve in FIG. 6, segments 338 of annular scaffold 332 protrude radially outward from heart valve prosthesis 100 to easily conform to calcified anatomy of the native valve while impermeable membrane 340 provides a mechanical barrier to the blood flowing through any gaps or cavities/crevices present between the heart valve prosthesis and the native valve tissue. Antegrade blood flow BF is illustrated by directional arrows in FIG. 6. Annular scaffold 332 is radially and circumferentially compliant due to its relatively small wire size, as described herein. With such maximized conformability, anti-paravalvular leakage component 330 functions as a continuous circumferential seal around the heart valve prosthesis to prevent or block blood flow between the outer surface or perimeter of the heart valve prosthesis and a native heart valve annulus.

In the embodiment of FIGS. 3-6, anti-paravalvular leakage component 330 is coupled to outer surface 103 of heart valve prosthesis 100 adjacent to second end 118 thereof. When deployed, anti-paravalvular leakage component 330 may be positioned in situ at the native valve annulus, slightly above the valve annulus, slightly below the valve annulus, or some combination thereof. Since the annular anti-paravalvular leakage component is coupled to outer surface 103 of heart valve prosthesis 100, longitudinal placement and/or the size and shape thereof is flexible and may be adjusted or adapted according to each application and to a patient's unique needs. For example, depending on the anatomy of the particular patient, the anti-paravalvular leakage component may be positioned on heart valve prosthesis 100 so that in situ the anti-paravalvular leakage component is positioned between heart valve prosthesis 100 and the interior surfaces of the native valve leaflets, between heart valve prosthesis 100 and the interior surfaces of the native valve annulus, and/or between heart valve prosthesis 100 and the interior surfaces of the left ventricular outflow track (LVOT).

Figure 8:
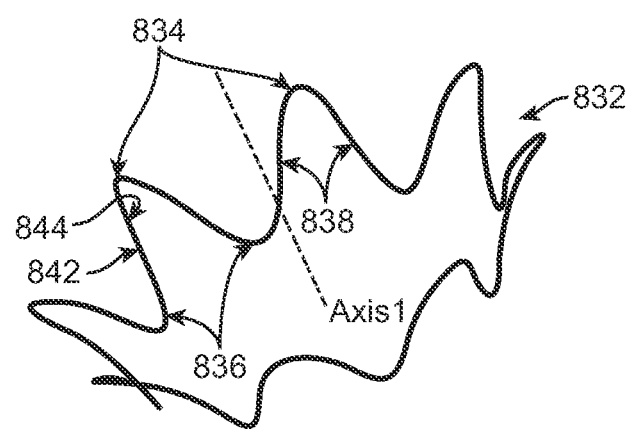
FIG. 8 is a perspective view of an annular scaffold for use in an anti-paravalvular leakage component, according to another embodiment hereof, wherein the annular scaffold includes peaks that curve or bow radially outward.

The shape or configuration of the annular scaffold may be optimized based on the design and application of the heart valve prosthesis. In another embodiment hereof depicted in FIGS. 8 and 9, an annular scaffold 832 includes segments 838 that curve or flare radially outward between valleys 836 that bend or curve radially inward for attachment to a stent of a heart valve prosthesis and peaks 834 that flare or curve radially outward. Outer surface 842 of each segment 838 is concave, while an inner surface 844 of each segment 838 is convex. Since only valleys 834 are coupled/constrained to the heart valve prosthesis and peaks 832 are unconstrained or free and highly flexible, annular scaffold 832 has an ability to conform to an outer sheath utilized in deployment thereof as described above.

Figure 9:
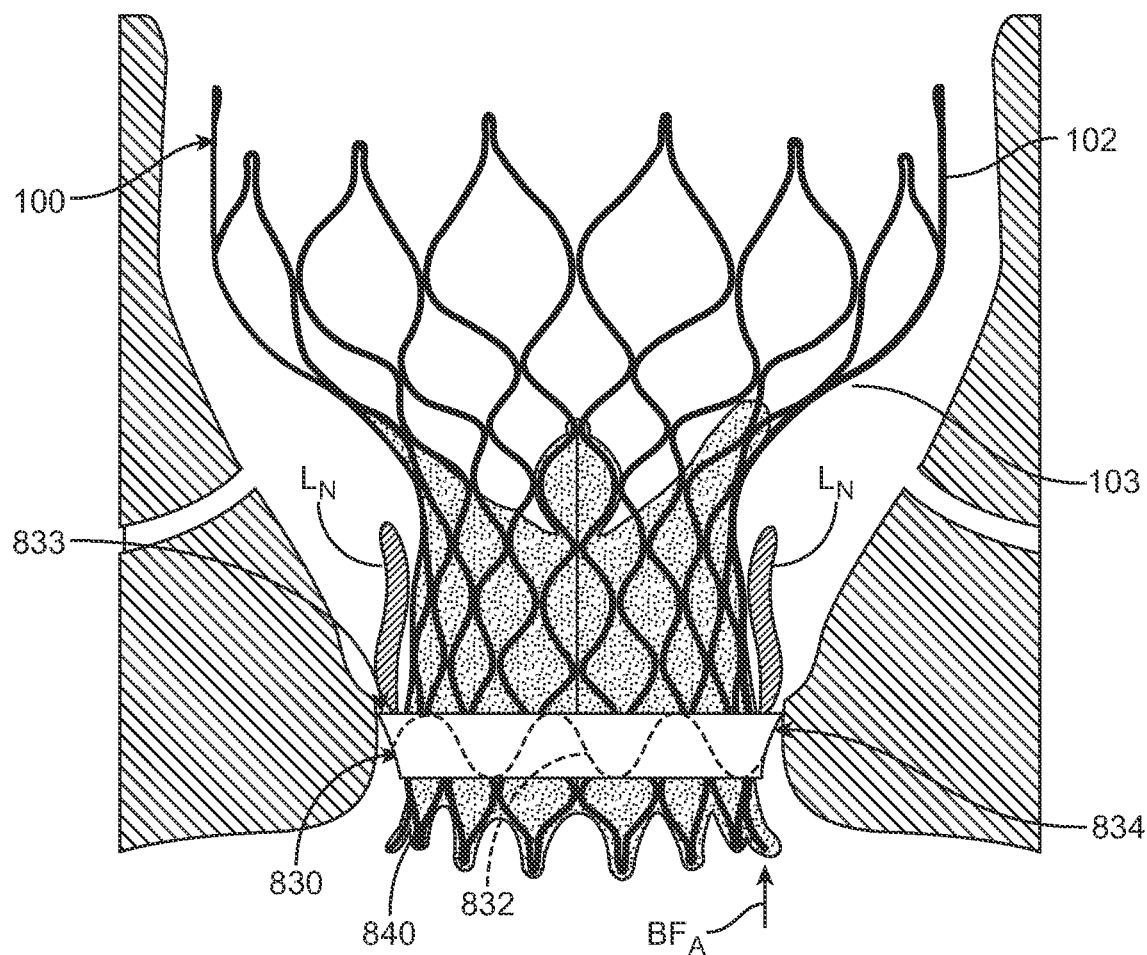
FIG. 9 is a side view illustration of an anti-paravalvular leakage component which used the annular scaffold of FIG. 8 implanted within a native valve annulus.

FIG. 9 illustrates an anti-paravalvular leakage component 830 coupled to heart valve prosthesis 100, which is deployed within an aortic valve having native valve leaflets LN. Anti-paravalvular leakage component 830 includes an impermeable membrane 840 coupled to an outer surface of annular scaffold 832, thereby forming an open-ended pocket or compartment 833 around stent 102 between an inner surface of anti-paravalvular leakage component 830 and outer surface 103 of heart valve prosthesis 100. Open-ended pocket 833 catches and blocks any retrograde flow within the aortic valve, thereby preventing undesired regurgitation and preventing blood stagnation in and around the native valve sinuses. In addition, the configuration of anti-paravalvular leakage component 830, formed by flared, unconstrained peaks 834 and impermeable membrane 840 coupled to the outside surface of the annular scaffold, diverts or deflects antegrade blood flow away from heart valve prosthesis 100. Antegrade blood flow $BF_A$ is illustrated with a directional arrow in FIG. 9. By diverting or deflecting antegrade blood flow away from the heart valve prosthesis and catching retrograde blood flow with open-ended pocket 833, anti-paravalvular leakage component 830 formed with annular scaffold 832 functions as a continuous circumferential seal around the heart valve prosthesis to prevent or block blood flow between the outer surface or perimeter of the heart valve prosthesis and a native heart valve annulus.

Figure 10:
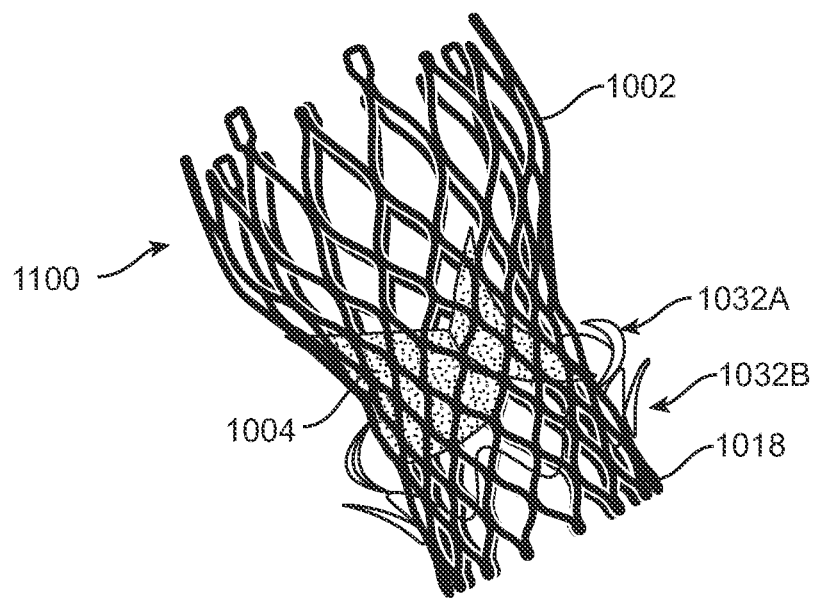
FIG. 10 is a perspective view of an annular scaffold for use in an anti-paravalvular leakage component, according to another embodiment hereof, wherein the annular scaffold includes a combination of peaks that curve radially inward and peaks that curve radially outward.

In yet another embodiment hereof, the anti-paravalvular leakage component may include two or more adjacent annular scaffolds. The adjacent annular scaffolds may have the same configuration, i.e., two adjacent annular scaffold 332 or two adjacent annular scaffold 832, or the adjacent annular scaffold may have different configurations. For example, FIG. 10 illustrates a heart valve prosthesis 1000 having a first annular scaffold 1032A and a second annular scaffold 1032B. Heart valve prosthesis 1000 includes a support frame or stent 1002 and a valve component 1004 secured therein, but graft material adjacent to a second end 1018 thereof is not shown for sake of clarity. Annular scaffold 1032A is similar to annular scaffold 332 and includes segments that bow or bulge radially outward while both peaks and valleys thereof bend or curve radially inward toward heart valve prosthesis 1000. Annular scaffold 1032B is similar to annular scaffold 832 and includes segments that are curved or flare radially outward between valleys that bend or curve radially inward for attachment to heart valve prosthesis 1000 and unconstrained peaks that flare or curve radially outward. Although not shown for sake of clarity, an impermeable membrane is coupled to each of annular scaffolds 1032A, 1032B to form two anti-paravalvular leakage components as described herein with respect to annular scaffolds 332, 832, respectively. In addition, although shown with annular scaffold 1032B adjacent to second end 1018 of heart valve prosthesis 1000, it will be apparent to one of ordinary skill in the art that annular scaffold 1032A may alternatively be located closer to second end 1018 than annular scaffold 1032B. The adjacent annular scaffolds may be positioned such their peaks and valleys are in phase with each other, or out of phase with each other for improved compressibility/collapsibility.

Figure 11:
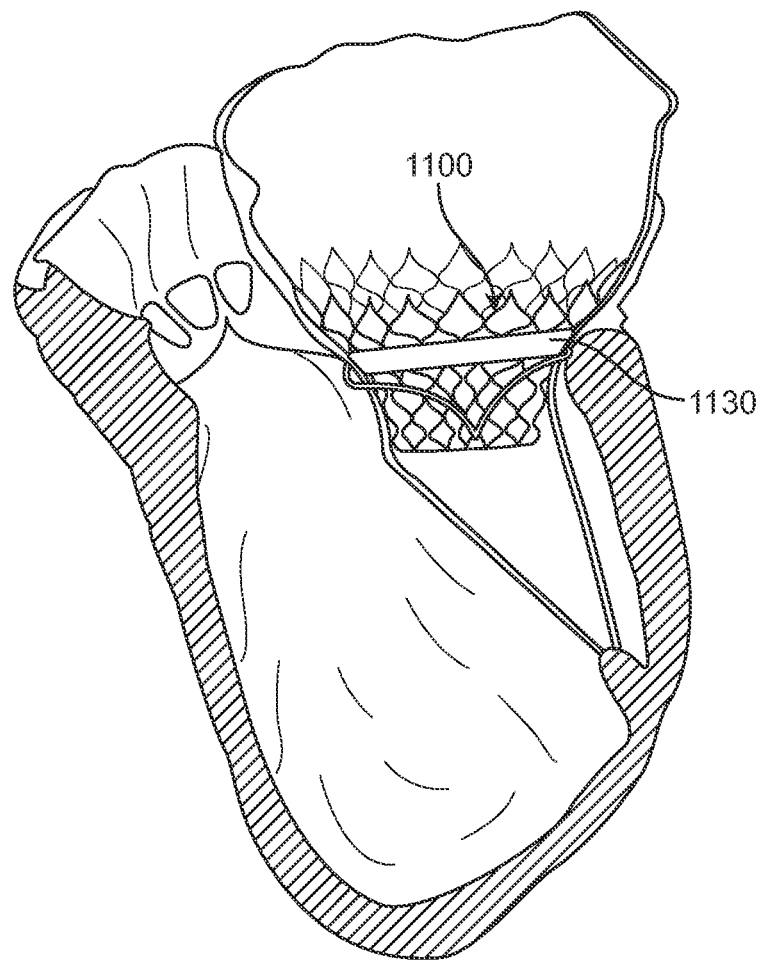
FIG. 11 is a side view illustration of a heart valve prosthesis, having an anti-paravalvular leakage component coupled thereto, implanted within a native mitral valve annulus.

Although embodiments depicted herein illustrate an anti-paravalvular leakage component integrated onto a heart valve prosthesis configured for implantation within an aortic valve, it would be obvious to one of ordinary skill in the art that an anti-paravalvular leakage component as described herein may be integrated onto a heart valve prosthesis configured for implantation implanted within other heart valves. For example, FIG. 11 illustrates an anti-paravalvular leakage component 1130 coupled to the outer surface or perimeter of a heart valve prosthesis 1100 implanted within a mitral valve.

Figure 12:
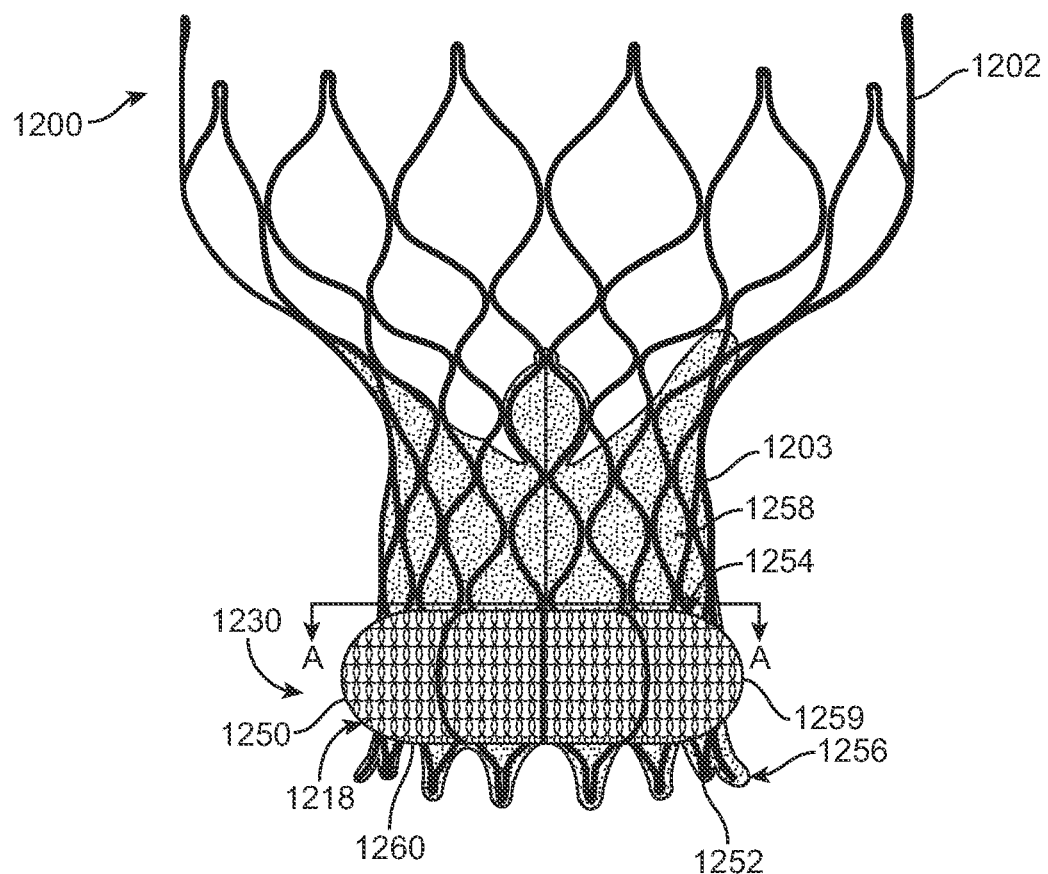
FIG. 12 is a side view of a heart valve prosthesis having an anti-paravalvular leakage component coupled thereto according to another embodiment hereof, wherein the anti-paravalvular leakage component includes a plurality of self-expanding segments and an annular sealing element coupled to an inside surface of the segments.

FIG. 12 illustrates an anti-paravalvular leakage component 1230, in its expanded or deployed configuration, coupled to a heart valve prosthesis 1200 according to another embodiment hereof. In this embodiment, anti-paravalvular leakage component 1230 includes a plurality of independent, self-expanding segments 1250 and an annular sealing element 1260. Annular sealing element 1260 is coupled to inner surfaces 1252 of segments 1250, and when the segments radially expand or deploy as described in more detail herein, annular sealing element 1260 is positioned between an outer surface 1203 of heart valve prosthesis 1200 and inner surfaces 1252 of the segments. As such, annular sealing element 1260 extends around the outer surface or perimeter of heart valve prosthesis 1200 and extends into and substantially fills any/all gaps or cavities/crevices between outer surface 1203 of heart valve prosthesis 1200 and native valve tissue to prevent paravalvular leakage in situ. In an embodiment hereof, annular sealing element 1260 may be formed from a swellable material that collapses easily and expands to a larger volume after implantation, such as but not limited to hydrogel or a collagen foam/sponge similar to the material commercially available under the trademark Angioseal. Other suitable material examples for annular sealing element 1260 include tissue, compressible foam materials, fabric, or compressible polymeric materials.

Figure 12A:
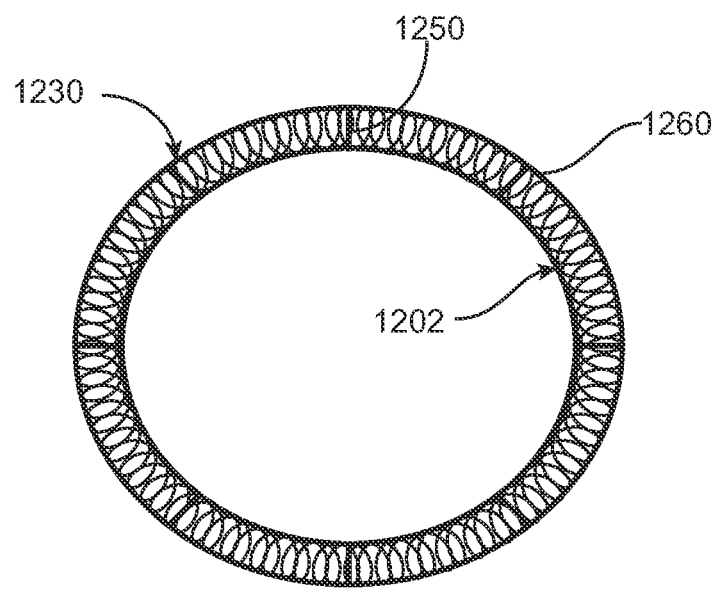
FIG. 12A is an end view of FIG. 12 taken along line A-A of FIG. 12.

Segments 1250 are coupled to an outer surface 1203 of heart valve prosthesis 1200. More particularly, first and second ends 1254, 1256 of segments 1250 are coupled to an outer surface 1203 of heart valve prosthesis 1200 via welding, sutures, or other suitable mechanical method. In another embodiment hereof, segments 1250 may be integrally formed with stent 1202 of heart valve prosthesis 1200. Segments 1250 are spaced apart in approximately equal intervals or segments around heart valve prosthesis 1200 as shown in FIG. 12A, which is an end view taken along line A-A of FIG. 12. In another embodiment hereof, the segments may be spaced apart in non-equal intervals or segments around the outside of the heart valve prosthesis. For example, it may be desirable to position one or more segments at a location on the heart valve prosthesis corresponding to an area prone to leakage in situ, such as adjacent to the native valve commissures. Although shown with eight segments 1250, it will be understood by one of ordinary skill in the art that a greater or lesser number of segments may be utilized herein.

As best shown in FIG. 13, in which annular sealing element 1260 has been removed for clarity, ends 1254, 1256 of each segment 1250 are coupled to opposing peaks or apexes of a diamond-shaped opening 1258 of stent 1202 of heart valve prosthesis 1200. In this embodiment, segments 1250 are coupled to diamond-shaped openings adjacent to end 1218 of heart valve prosthesis 1200 but it will be understood that the segments may be coupled to diamond-shaped openings anywhere along the length of stent 1202. The longitudinal position of anti-paravalvular leakage component 1230 on heart valve prosthesis 1200 may vary depending upon application and configuration of the heart valve prosthesis. Coupling each segment 1250 to opposing peaks or apexes of a diamond-shaped opening 1258 of stent 1202 allows each segment to utilize the foreshortening of stent 1202 to its advantage because each segment 1250 aligns and packs/collapses within its corresponding opening 1258 when heart valve prosthesis 1200 is crimped for delivery. More particularly, as shown in FIG. 14, when heart valve prosthesis 1200 is crimped onto a catheter (not shown) for delivery thereof, openings 1258 are longitudinally stretched and elongate to a length L2, which is shown in FIG. 14A. An arc length of each segment 1250 is approximately equal to length L2, the crimped length of opening 1258 such that each segment 1250 is stretched flat or flush over its corresponding opening 1258 when crimped. Stated another way, each segment 1250 is straightened when heart valve prosthesis 1200 is crimped for delivery and the straightened segment 1250 is in line or flush with the crimped stent 1202. When each segment 1250 is stretched flat or flush over its corresponding opening 1258, the material of annular sealing element 1260 is compressed and pulled inside stent 1202 via openings 1258. Accordingly, the additional of anti-paravalvular leakage component 1230 advantageously does not increase, or minimally increases, the packing profile of heart valve prosthesis 1200 so that heart valve prosthesis 1200 has the ability to pack in lower profile delivery systems.

When heart valve prosthesis 1200 is deployed, as shown in FIG. 13, stent 1202 foreshortens and the length of openings 1258 return to their deployed length $L_1$, which is shown in FIG. 13A. Segment 1250, and annular sealing member 1260 attached thereto, self-expand radially outward as shown in FIG. 12 and FIG. 13. An outer surface 1259 of each segment is convex, while the inner surface 1252 of each segment is concave. Similar to segments 338 of annular scaffold 332 described with respect to FIG. 6 herein, segments 1250 bow or curve radially outward to easily conform to calcified anatomy of the native valve while annular sealing member 1260 provides a mechanical barrier to the blood flowing through any gaps or cavities/crevices present between the heart valve prosthesis and the native valve tissue. In this embodiment, since annular sealing member 1260 is positioned between segments 1250 and prosthesis 1200, the sealing member is protected from being unintentionally moved or shifted during delivery.

Similar to previous embodiments described herein, anti-paravalvular leakage component 1230 may be formed concurrently with or subsequent to heart valve prosthesis 1200 and each segment 1250 of anti-paravalvular leakage component 1230 may be formed from a wire that may be solid or hollow and may have a different cross-section and/or size from stent 1202 of heart valve prosthesis 1200. For example, segments 1250 may be formed of a relatively thinner or smaller wire as compared to a strut of stent 1202 such that anti-paravalvular leakage component 1230 has greater flexibility to conform to the inner surface of the native valve annulus including any surface irregularities that may be present, thereby filling any gaps or cavities/crevices that may be present between the heart valve prosthesis 1200 and native tissue, while the thicker struts of stent 1202 provide sufficient radial force to deploy the heart valve prosthesis into apposition with the native valve annulus.

Segments 1250 are radially-compressible and self-expanding. In order to self-expand, segments 1250 may be made from a metallic material having a mechanical memory to return to the preset expanded or deployed shape. Mechanical memory may be imparted to segments 1250 by thermal treatment to achieve a spring temper in stainless steel, for example, or to set a shape memory in a susceptible metal alloy, such as NiTi (Nitinol) or Co—Cr (Cobalt-Chrome). In an alternate embodiment, a mechanical memory to return to the preset expanded or deployed shape may be imparted to a shape memory polymer that forms segments 1250, such as any of the polymers disclosed in U.S. Pat. Appl. Pub. No. 2004/0111111 to Lin, which is herein incorporated by reference in its entirety.

Figure 15:
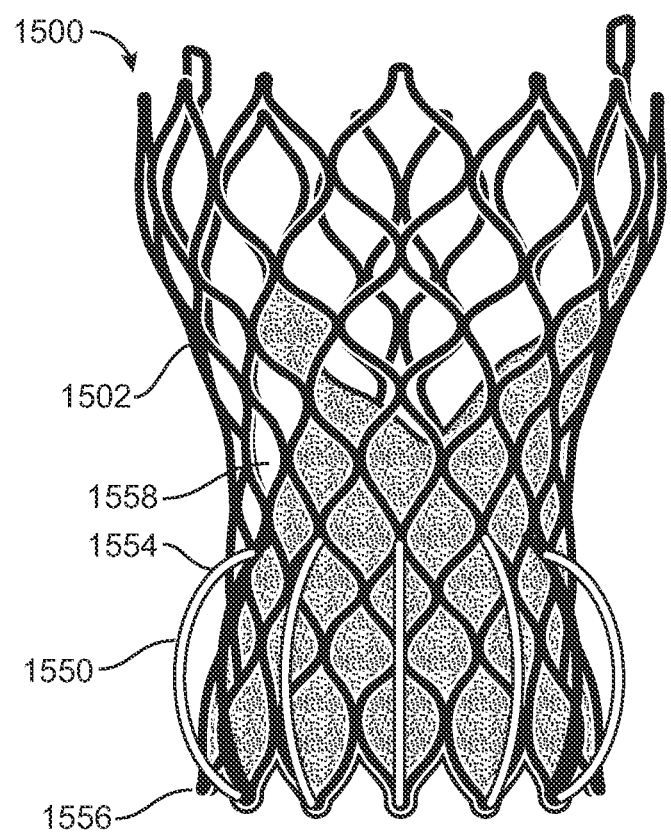
FIG. 15 is a side view of a heart valve prosthesis having an anti-paravalvular leakage component coupled thereto according to another embodiment hereof, wherein the anti-paravalvular leakage component includes a plurality of self-expanding segments that extend over two longitudinally adjacent diamond-shaped openings of a stent.
Figures 15A, 15B:
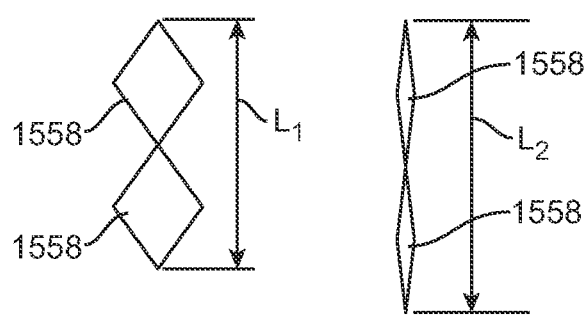
FIG. 15A illustrates the length of a diamond-shaped opening of a stent when the heart valve prosthesis of FIG. 15 is in a deployed or expanded configuration.
FIG. 15B illustrates the length of a diamond-shaped opening of a stent when the heart valve prosthesis of FIG. 15 is in a compressed or delivery configuration.

It will be understood by one of ordinary skill in the art that the length of anti-paravalvular leakage component 1230 is not limited to the embodiment shown in FIG. 12. For example, as shown in the embodiment of FIG. 15, in which the annular sealing element has been removed for clarity, each segment 1250 may extend over two openings 1558 of a stent 1502 of a heart valve prosthesis 1500. Ends 1554, 1556 of each segment 1550 are coupled to opposing peaks or apexes of two longitudinally-adjacent diamond-shaped opening 1558. As explained above, each segment 1550 aligns and packs/collapses within its corresponding openings 1558 when heart valve prosthesis 1500 is crimped for delivery. An arc length of each segment 1550 is approximately equal to length L2, the crimped length of two longitudinally-adjacent diamond-shaped openings 1558, as shown in FIG. 15B. When heart valve prosthesis 1500 is deployed, as shown in FIG. 15, stent 1502 foreshortens and the length of two longitudinally-adjacent diamond-shaped openings 1558 return to their deployed length $L_1$, which is shown in FIG. 15A. Segment 1550, and the annular sealing member attached thereto, self-expand or bow radially outward to conform to the anatomy of the native valve.

Figure 16:
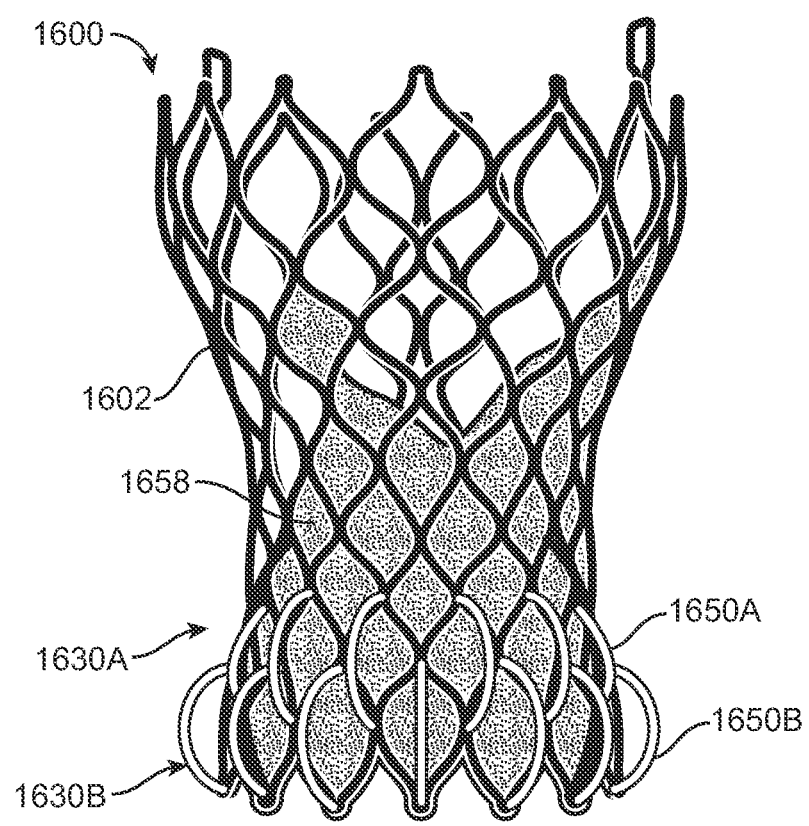
FIG. 16 is a side view of a heart valve prosthesis having two anti-paravalvular leakage components coupled thereto according to another embodiment hereof.

In addition, two or more anti-paravalvular leakage components may be included on a heart valve prosthesis. For example, FIG. 16 illustrates a heart valve prosthesis 1600 having a first anti-paravalvular leakage component 1630A and a second anti-paravalvular leakage component 1630B. Although not shown for sake of clarity, an annular sealing element is coupled inside surfaces of segments 1650A, 1650B to form two anti-paravalvular leakage components 1630A, 1630B, respectively, as described herein with respect to anti-paravalvular leakage component 1230. Segments 1650A, 1650B are shown coupled to adjacent rows of openings 1658 of stent 1602 such that anti-paravalvular leakage components 1630A, 1630B are abutting against each other, but anti-paravalvular leakage components 1630A, 1630B may alternatively be positioned at longitudinally spaced apart locations on heart valve prosthesis 1600.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
   a tubular stent having a compressed configuration for delivery within a vasculature and an expanded configuration for deployment within a native heart valve;
   a prosthetic valve component disposed within and secured to the stent; and
   an anti-paravalvular leakage component including a plurality of self-expanding segments and an annular sealing element coupled to inner surfaces of the segments, a first end and a second end of each segment being coupled to an outer surface of the tubular stent, wherein the anti-paravalvular leakage component has an expanded configuration in which the segments curve radially away from the outer surface of the tubular stent and the annular sealing element is positioned between the outer surface of the tubular stent and inner surfaces of the segments.

2. The transcatheter valve prosthesis of claim 1, wherein the segments are spaced apart in approximately equal intervals around the tubular stent.

3. The transcatheter valve prosthesis of claim 1, wherein the annular sealing element is formed from a swellable material that collapses easily and expands to a larger volume after implantation.

4. The transcatheter valve prosthesis of claim 1, wherein the annular sealing element is formed from a compressible foam.

5. The transcatheter valve prosthesis of claim 1, wherein the first and second ends of each segment are coupled to opposing peaks of a diamond-shaped opening formed within the tubular stent.

6. The transcatheter valve prosthesis of claim 5, wherein an arc length of each segment is approximately equal to a crimped length of the diamond-shaped opening.

7. The transcatheter valve prosthesis of claim 1, wherein each segment is formed from a wire that has a different cross-section and/or size from a strut of the tubular stent.

8. The transcatheter valve prosthesis of claim 7, wherein the wire that forms the segments is thinner than the strut of the tubular stent.

9. The transcatheter valve prosthesis of claim 8, wherein the wire that forms the segments has a circular cross-section and the strut of the tubular stent is non-circular.

* * * * *